United States Patent [19]
Stambaugh et al.

[11] Patent Number: 5,919,200
[45] Date of Patent: Jul. 6, 1999

[54] BALLOON CATHETER FOR ABRADING A PATENT FORAMEN OVALE AND METHOD OF USING THE BALLOON CATHETER

[75] Inventors: Bruce D. Stambaugh, Anaheim; Hien V. Nguyen, Santa Ana, both of Calif.

[73] Assignee: Hearten Medical, Inc., Tustin, Calif.

[21] Appl. No.: 09/169,142

[22] Filed: Oct. 9, 1998

[51] Int. Cl.⁶ .................................................. A61B 17/22
[52] U.S. Cl. ............................................................ 606/159
[58] Field of Search .................................. 606/159, 170, 606/167, 180; 623/1

[56] References Cited

U.S. PATENT DOCUMENTS

| | | | |
|---|---|---|---|
| 5,320,634 | 6/1994 | Vigil et al. | 606/159 |
| 5,336,234 | 8/1994 | Vigil et al. | 606/159 |
| 5,662,701 | 9/1997 | Plaia et al. | 623/1 |
| 5,665,098 | 9/1997 | Kelly et al. | 606/170 |

*Primary Examiner*—Michael Buiz
*Assistant Examiner*—Kevin Truong
*Attorney, Agent, or Firm*—Burns, Doane, Swecker & Mathis LLP

[57] ABSTRACT

The present invention provides a device and method for closing a patent foramen ovale. The present invention comprises a catheter sheath with proximal and distal ends. A balloon catheter with a plurality of abrasive members is deployably retained within the catheter sheath. Once the catheter sheath is placed by a treating health care professional across a patent foramen ovale, the balloon catheter is advanced such that the balloon and the abrasive members are deployed outside of the distal end of the catheter sheath. The catheter sheath is then removed from the foramen ovale and the balloon is inflated. The treating healthcare professional then abrades the inner surfaces of the patent foramen ovale to thereby cause an area of thrombogenesis. The balloon catheter is then deflated and the abrasive members are then repositioned into the distal end of the catheter sheath and then removed from the patient. The thrombogenic area created along the inner surfaces of the patent foramen ovale then creates of thrombus which over time turns into a scar and the foramen ovale is obliterated.

18 Claims, 4 Drawing Sheets

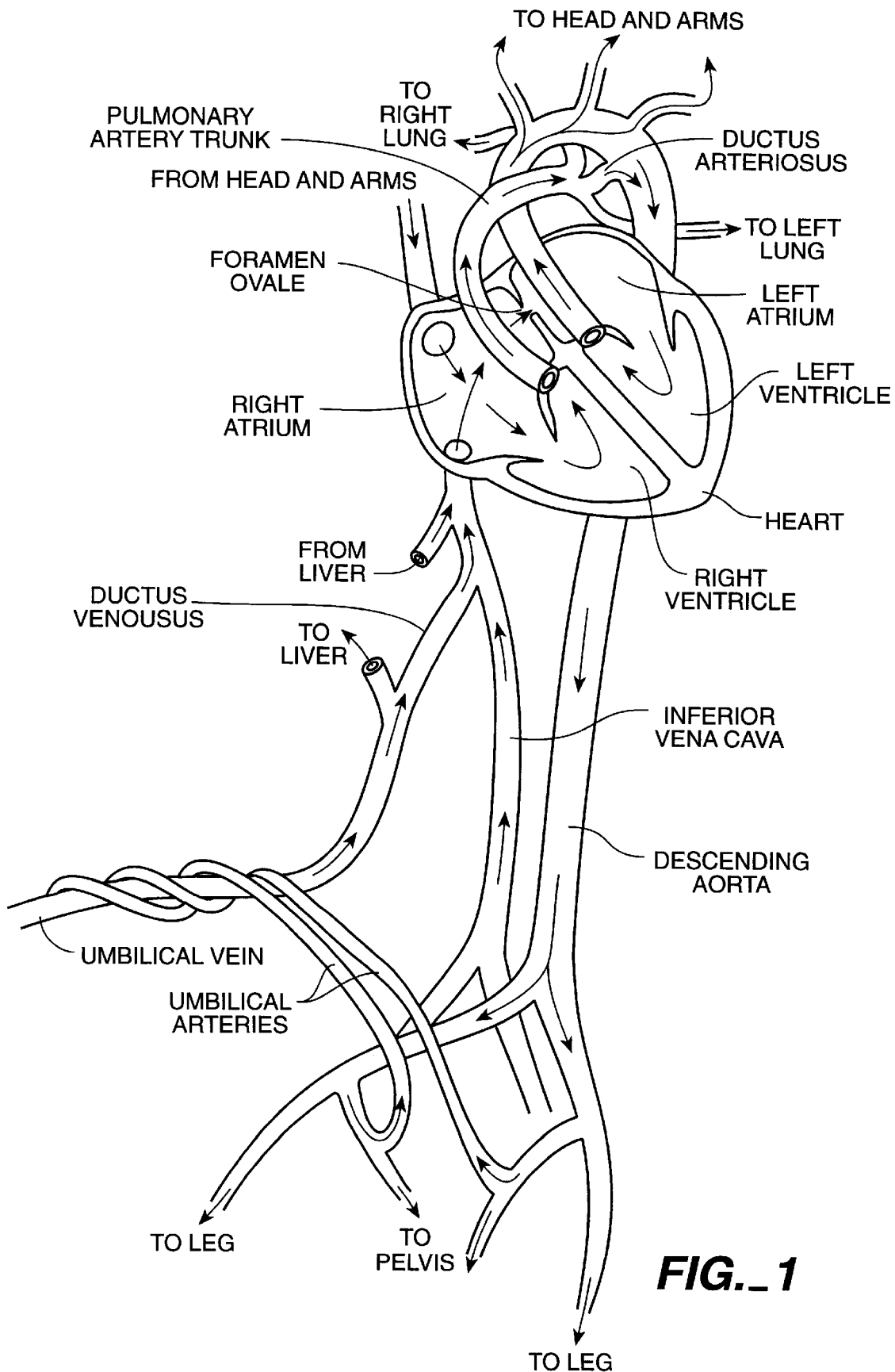
FIG._1

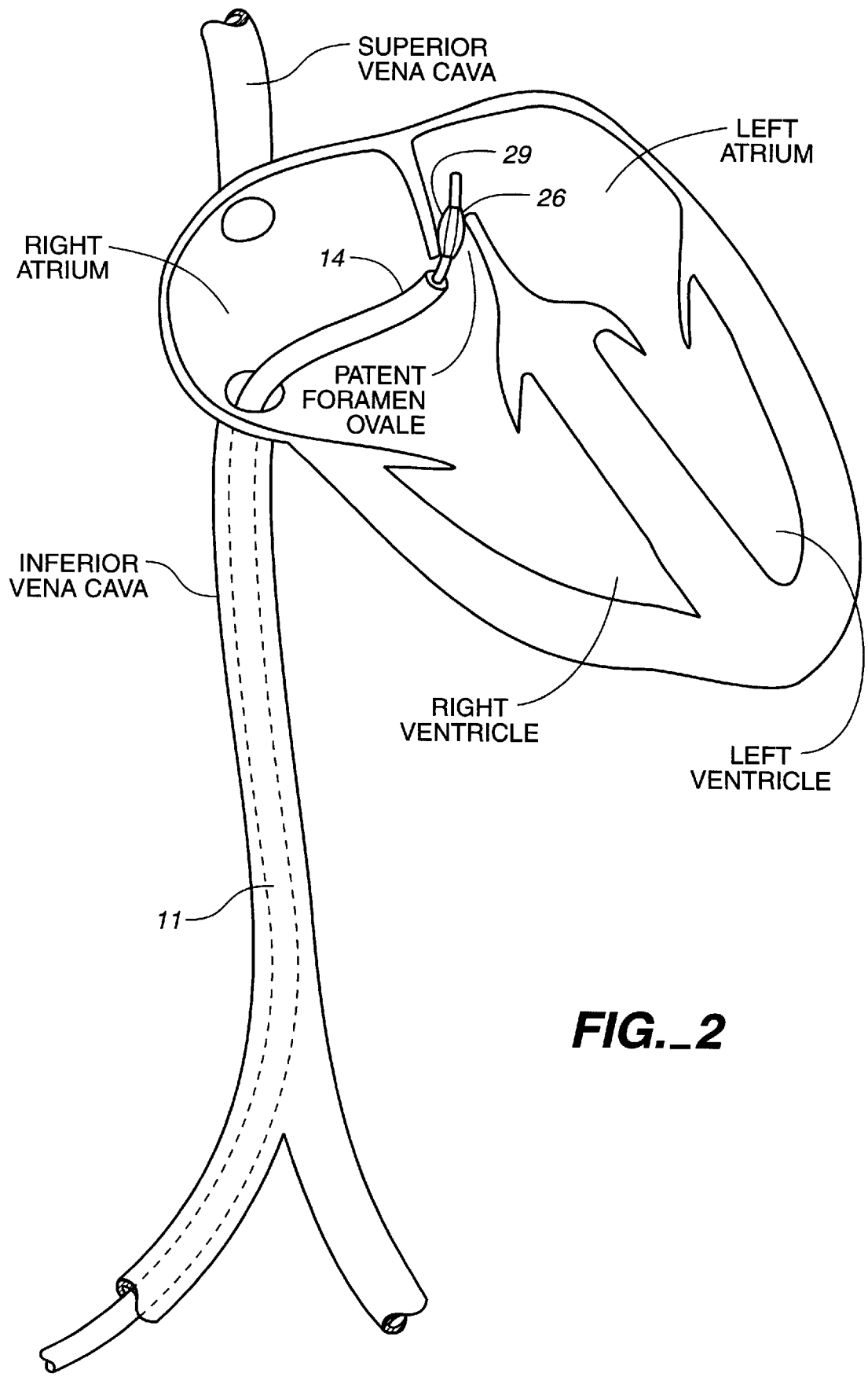
FIG._2

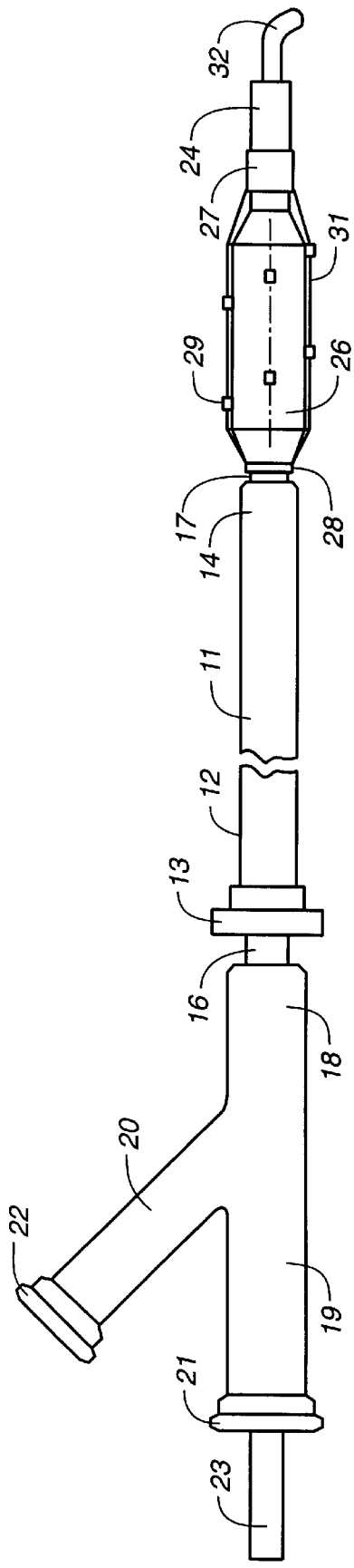
FIG._3
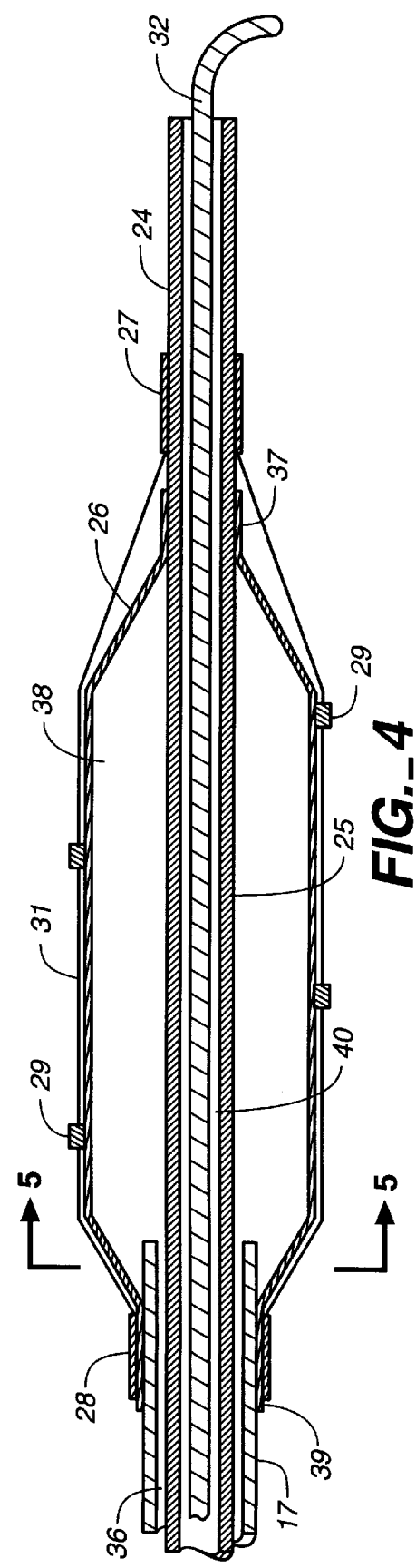
FIG._4

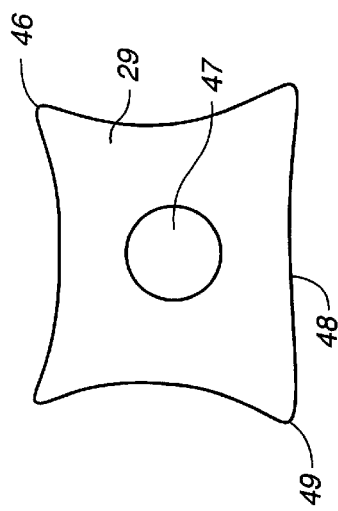
FIG._6
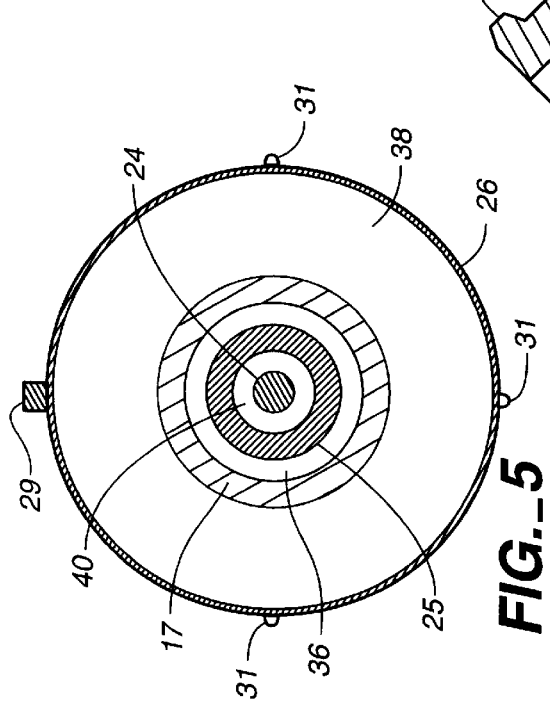
FIG._5
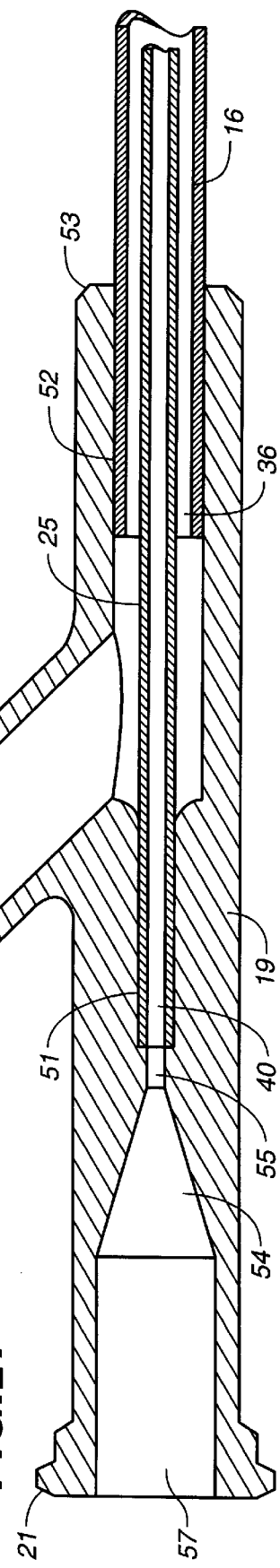
FIG._7

BALLOON CATHETER FOR ABRADING A PATENT FORAMEN OVALE AND METHOD OF USING THE BALLOON CATHETER

FIELD OF THE INVENTION

The present invention is related generally to medical/surgical devices that can be placed within the body of a patient to perform a procedure. More specifically, the present invention is a minimally invasive device useful in closing a patent foramen ovale.

BACKGROUND OF THE INVENTION

The fetal circulation is vastly different than the normal adult circulation. The blood circulating in a fetus is oxygenated by the placenta, not the developing lungs. Therefore, the fetal circulation directs only a small percentage of the circulating blood to the fetal lungs. Most of the circulating blood is shunted away form from the lungs to the peripheral tissues through specialized vessels and foramens that are open ("patent") during fetal life. In most people these specialized structures quickly close after birth, unfortunately, sometimes they fail to close and create hemodynamic problems that can be fatal if left untreated.

The fetal circulation is illustrated in FIG. 1. The umbilical arteries branch off of the iliac arteries and deliver unoxygenated (blue) blood to the placenta. The fetal blood travels through the capillary bed in the placenta and transfers carbon dioxide to the maternal blood and takes oxygen and other nutrients from the maternal blood. The umbilical vein returns oxygenated (red) blood to the fetus. Most of the oxygenated blood from the umbilical vein bypasses the developing liver and travels through a specialized vessel called the ductus venosus to the inferior vena cava and then into the right atrium. A good portion of the oxygenated blood from the inferior vena cava is directed across the right atrium and into the left atrium through a specialized curtain like opening in the heart called the foramen ovale. The blood from the left atrium then enters the left ventricle and then into the aorta where it travels to the head and other body tissues delivering the needed oxygen and nutrients.

The small amount of blood entering the right atrium that does not pass through the foramen ovale, most of which comes from the superior vena cava, flows into the right ventricle and then gets pumped into the pulmonary trunk and pulmonary arteries. Some of this blood is pumped into the developing lungs. However, the fetal lungs are collapsed which causes a high resistance to blood flow. Another specialized vessel, called the ductus arteriosus, is a vessel that connects the high pressure pulmonary artery to the lower pressure aorta. Therefore, most of the blood in the pulmonary artery flows into the lower pressure aorta through this specialized vessel.

Upon birth, the circulatory system goes through profound changes. The flow through the umbilical arteries and umbilical vein stops and consequently the flow through the musculature around the ductus venosus constricts and the blood flow through the ductus venosus stops. The lungs fill with air and the resistance to blood flow into the lungs drastically decreases. The corresponding pressure in the right atrium, right ventricle, and pulmonary arteries also decrease. The decrease in pressure in the right atrium causes the curtain like opening of the foramen ovale to close, driving more blood into the right ventricle and then to the lungs for oxygenation. Over time, the foramen ovale is replaced with a membrane called the fossa ovalis. Similarly, the decrease in pressure in the pulmonary arteries reduced the pulmonary arterial pressure to the same as or slightly less than the pressure in the aorta, which stops or reverses the flow through the ductus arteriosus. Once the muscular tissue of the ductus arteriosus is perfused with well oxygenated blood, the muscle begins to constrict and close the ductus arteriosus. The ductus arteriosus normally closes within about one week of life.

Usually over time, the unique openings of the fetal circulation become obliterated and a solid mass of tissue forms where these opening once were. However, in some people the openings remain. A patent ductus venosus after birth is very rare and almost always fatal. A patent ductus arteriosus occurs in about 1 out of every 5000 births. The patent ductus arteriosus once diagnosed is either medically treated or surgically ligated to close the ductus. In about one of four people, the foramen ovale does not seal shut, instead it remains patent. Since the pressure in the left atrium is about two to four mm Hg greater than the pressure in the right atrium, the curtain like opening usually remains shut. However, if the pressure in the right atrium increases, such as upon heavy lifting or while performing a Val Salva type maneuver, the curtain like fold of tissue opens and the blood flows from the right atrium to the left ventricle.

Studies have shown that adults with strokes of unknown origin (cryptogenic strokes) have about twice the normal rate of patent foramen ovales than the normal population. Although there is a correlation between strokes and patent foramen ovales, it is currently unknown why this correlation exists. Many people theorize that blood clots and plaque that have formed in the peripheral venous circulation (in the legs for example) break off and travel to the heart. Normally, the clots and plaque get delivered to the lungs where it is trapped and usually cause no harm to the patient. Patients with a patent foramen ovale, however, have a potential opening that the clots or plaque can pass through the venous circulation and into the arterial circulation and then into the brain or other tissues to cause a thromboembolic event like a stroke. The clots may pass to the arterial side when there is an increase in the pressure in the right atrium. Then the clots travel through the left side of the heart, to the aorta, and then to the brain via the carotid arteries where they cause a stroke and the associated neurological deficits.

Currently, the method of choice to close a patent foramen ovale is open heart surgery and ligation of the foramen ovale to close it. This obviously is associated with the usually risks of general anesthesia, open heart procedures, infections, etc. Another method is a catheter based method which places to opposing umbrella shaped devices around the foramen ovale, one in the right atrium and one in the left atrium. Unfortunately, this procedure is technically difficult and leaves behind two foreign objects that could dislodge or cause a thromboembolus which could break off and cause thromboembolic events. What is needed therefore is a least invasive method for closing a patent foramen ovale which does not have the associated risk of an open heart procedure, is technically easy to perform, and which does not leave any foreign material behind.

SUMMARY OF THE INVENTION

The present invention provides a device and method for closing a patent foramen ovale. The present invention comprises a catheter sheath with proximal and distal ends. A balloon catheter with a plurality of abrasive members is deployably retained within the catheter sheath. Once the catheter sheath is placed by a treating health care professional across a patent foramen ovale, the balloon catheter is advanced such that the balloon and the abrasive members are deployed outside of the distal end of the catheter sheath. The catheter sheath is then removed from the foramen ovale and the balloon is inflated. The treating healthcare professional then abrades the inner surfaces of the patent foramen ovale to thereby cause an area of thrombogenesis. The balloon catheter is then deflated and the abrasive members are then repositioned into the distal end of the catheter sheath and then removed from the patient. The thrombogenic area created along the inner surfaces of the patent foramen ovale then creates of thrombus which over time turns into a scar and the foramen ovale is obliterated.

BRIEF DESCRIPTION OF THE DRAWINGS

As used herein, like reference numerals will designate similar elements in the various embodiments of the present invention wherein:

FIG. 1 is a schematic diagram of the fetal circulation of a mammal;

FIG. 2 is a schematic diagram of a catheter of the present invention traveling up the inferior vena cava of a patient into the right atrium and through the foramen ovale;

FIG. 3 is a schematic plan view of a foramen ovale catheter of the present invention;

FIG. 4 is an axial cross-sectional view of the distal end of the catheter of FIG. 3;

FIG. 5 is a perpendicular cross-sectional view of the catheter of FIG. 3 taken along the plane indicated in FIG. 4 by line 5—5;

FIG. 6 is a plan end view of an abrasive member of the present invention; and

FIG. 7 is an axial cross-sectional view of the proximal end of the present invention.

DETAILED DESCRIPTION OF THE PREFERRED EMBODIMENTS

The present invention provides a novel least invasive device and method for closing a patent foramen ovale in a mammal. The device is specifically designed to be used in catheterization laboratories in hospitals for treating humans as well as veterinary hospitals for treating animals. As used herein the term "patient" shall refer to human patients as well as animal patients. As illustrated in FIG. 2, the device is introduced into the blood stream using well known catheterization procedures. The device is initially introduced within a catheter sheath 11 with a distal end 14. The device then extends distally from the catheter sheath to span the patent foramen ovale. The device has a plurality of abrasive members 29 attached over an inflatable balloon 26. The balloon is inflated while in the foramen ovale and the abrasive members are forced into interior tissue of the foramen ovale. The operator of the device can then remove endothelial cells and create trauma to the area by rotating and moving the device. The balloon is then deflated and then the device is retracted into the catheter sheath. The device is then removed from the patient. Once the endothelium has been removed and the area inside the patent foramen ovale has been traumatized, the body's healing mechanism begins. Because the pressure within the left atrium is greater than the pressure in the right atrium, the curtains of tissue that comprises the patent foramen ovale are directly opposed to each other. The body's healing mechanism then replaces the traumatized tissue with scar tissue and the scar tissue forms across the curtain of tissue permanently sealing the foramen ovale. Over time, the foramen ovale becomes completely obliterated and turns into the normal fossa ovalis.

Turning now to FIG. 3, the foramen ovale catheter of the present invention is further illustrated. In order to obtain access to the blood stream, the patent foramen catheter has to be advanced through the skin of the patient into a blood vessel, preferably a standard femoral vein catheterization is used that is well known in the art, however other vessel access to the atriums can be used. Typically, a standard introducer is used to gain access from the skin of the patient to the lumen of the vessel. These introducers are commercially available from many different manufacturers, Cordis Corporation of Miami Fla. being one, Cook of Bloomington Ind. being another. The introducer can be of many different sizes, in the preferred embodiment the introducer varies from a 6 French to a 15 French introducer. Presently it is preferred to use a 7 or 8 French introducer.

A sheath catheter 11 is then advanced through the catheter port of the introducer. The outer diameter of the sheath catheter can vary from about 5 French to about 15 French. The inner diameter is such that a 4 French to about a 14 French foramen ovale catheter can be placed within its lumen. In the preferred embodiment, the sheath catheter is a single lumen catheter made by extruding standard catheter materials using standard extrusion techniques. Currently it is preferred to extrude polyether-block-amide, nylon, polyurethane, polyimide, or a polyolefin copolyester. However, any other extrudable catheter material well known in the art can be used to manufacture the catheter. The smaller the catheter, the stronger the extruding material should be. With very small catheters, the catheter can be reenforced by using braided meshing, a technique already well known in the catheter arts. The catheter has a proximal end 12 and a distal end 14. Provided at the proximal end is a port access 13 which allows the balloon catheter to be introduced through the sheath catheter. The sheath catheter's length is such that it can easily be used from a femoral site to reach an atrium of the heart, about 80 to 140 cm, with about 120. cm being preferred. Optionally, the distal end of the sheath catheter can have a radio-opaque marker 24 such as a metallic ring placed around the distal end or incorporated into the distal end such that the distal end is visible under imaging techniques such as fluoroscopy.

Inserted inside the sheath catheter's lumen is a foramen ovale balloon catheter 16 of the present invention. The catheter has a proximal end 18 provided with a standard "Y" fitting 19 and a distal end 24. The Y fitting comprises a standard port 21 for the placement of a guide wire 23. The guide wire can be any standard guide wire in the industry. Typically, the guide wire is made out of a coil and has a blunt distal end 32 to prevent damage to vessels when the catheter is advanced. The angled stem 20 of the Y fitting is provided with a lure lock type fitting 22 which is used to control the amount of fluid in the catheter to inflate and deflate the balloon. Typically a syringe is connected to the port to allow for the inflation and deflation of the balloon.

Located at the distal end of the foramen ovate balloon catheter is the balloon 26. Referring now to FIGS. 3–5, the foramen ovale catheter is actually comprised of two catheters, the outer catheter 16 which is placed within the catheter sheath, and an inner catheter 25 which has a lumen 40 for the guide wire 23. The inner catheter is longer than the outer catheter, the length corresponding to the length of the balloon (about 1 to 2 cm) plus an additional amount for the movement of the free floating ring 27 that is bonded to the wires 31 that cover the balloon. The outer and inner catheters can be made by extruding standard catheter materials using standard extrusion techniques, just like the sheath catheter. The outer catheter typically has an outer diameter of about 6 French to about 14 French, with 8 French being presently preferred. Between the outer and inner catheter is an area 36 for fluid to communicate with the fluid port and the interior of the balloon. The inner catheter is sized to fit within the outer catheter leaving adequate room for the fluid space 36. Currently the inner catheter has an outer diameter of about 3 French to about 12 French with 6 French being presently preferred. The balloon 26 is bonded to the distal end 17 of the outer catheter with an appropriate adhesive 39 such as heat curable polyurethane and the like. The balloon is also bonded near the distal end 24 of the inner catheter using an adhesive 37. This creates the fluid cavity 38 of the balloon.

The balloon can be made of any standard medical grade balloon material such as latex, polyurethane, and the like. Currently it is preferred that the balloon is somewhat non-compliant and thus a balloon manufactured from poly-ethylene-terephthalte ("PET") or nylon is presently preferred. The balloon can vary in length from about 5 mm to about 25 mm with 10 mm being presently preferred. The balloon's diameter can also vary from about 3 mm to about 20 mm, with diameters of 4, 6, 8, 10, and 12 mm being presently preferred.

Covering the balloon are a plurality of wires. The wires can be made out of any suitable material such as stainless steel, a nickel-titanium-alloy, and the like. The wires are anchored at the proximal end with a metallic ring 28 the is bonded over the proximal end of the balloon. The distal end of the wires are also bonded to a ring 27, however this ring is free floating over the distal end of the inner catheter to allow for the movement of the ring when the balloon is inflated and deflated. The wires can be rectangular in cross section such that the wire are themselves abrasive. Optionally, attached to the wires are abrasive members 29. The abrasive members can be any suitable member that causes abrasion to the inner surface of a foramen ovale. Examples of suitable abrasive members are drops of glue, metal cylinders bonded to the wires, plastic cylinders bonded to the wires, and the like. Referring now to FIG. 6, a presently preferred abrasive member is illustrated. The abrasive member is somewhat rectangular in shape, with the walls of the rectangle being concave such that the top corners 46 come to a sharp point. The bottom corners 49 of the abrasive members are rounded off to prevent damage to the balloon when the foramen ovale catheter is abrading tissue. The center of the abrasive member is provided with a hole 47 for placing over the wire.

Turning now to FIG. 7, a preferred Y type fitting 19 is illustrated. The proximal end of the outer catheter 16 is bonded to the distal end 53 of the Y fitting with bonding material 52. The inner catheter extends proximally past the fluid port 20 and is bonded in the middle of the Y fitting with bonding material 51. Thus, as can be appreciated by the drawing, the lumen 58 of the fluid port is in direct communication with the fluid space 36 between the inner and outer catheters. The guide wire port 57 at the most proximal end of the Y fitting is slightly tapered. The taper then increases to a conical section 54 until the inner diameter 55 is about identical to the inner diameter of the inner catheter. The tapering makes it easy to place the guide wire through the lumen 40 of the inner catheter.

Those acquainted with medical procedures will appreciate that any medical procedure involving the heart should be practiced only by health care professionals with extensive training and experience in cardiology and/or cardiac surgery. Therefore the present invention provides for a method of training a person to perform the procedure of abrading a patent foramen ovale using the disclosed embodiments. The method of training includes the steps of demonstrating the device, supervising the person being trained, and the labeling instructions included with the device on when and how to use the device.

The embodiments of the present invention are all used similarly. Fist the shape and size of the foramen ovale is determined using standard imaging techniques such as magnetic resonance imaging, trans-esophageal echocardiography, and the like. Once the shape and size is determined, an appropriate sized balloon can be used to fill the inside of the patent foramen ovale. Then, access is gained to a blood vessel. Typically the femoral vein is catheterized using any one of may commercially available introducing catheters that are well known in the art. Once the introducing catheter is in place, a single lumen catheter that is long enough to reach the foramen ovale and is large enough to allow the particular embodiment of the present invention to pass through the lumen is placed through the introducing catheter. An example of this type of catheter is the 8 French Mullins Introducer Set manufactured by Cook of Bloomington Ind. Typically these catheters are provided with a fairly stiff guide wire to allow for probing the right atrium for the foramen ovale. The single lumen catheter is advanced to the right atrium and then through the foramen ovale to the left atrium.

Next the guide wire is removed and the foramen ovale catheter is advanced in the single lumen catheter to the left atrium. The single lumen catheter is then removed from the left atrium and the foramen ovale.

The balloon catheter is then placed within the foramen ovale by slowly withdrawing the catheter back from the left atrium towards the right atrium. The balloon is then inflated with a fluid, typically either saline, water, or air. Once the balloon is inflated, the foramen ovale catheter is then slowly pulled back through the foramen ovale to abrade the interior of the foramen ovale. Usually the foramen ovale catheter is rotated while passing through the foramen ovale to enhance the abrasions being made. After the interior is abraded, the balloon is deflated and the foramen ovale catheter is then withdrawn into the single lumen catheter and then removed from the patient. All the catheters are then removed and the puncture site is sealed using standard techniques.

The abrasions created within the foramen ovale start a healing process which over time seals the foramen ovale shut with scar tissue. Once the foramen ovale is shut, the patient no longer has the risks associated with an patent foramen ovale.

While several particular embodiments of the invention have been illustrated and described, it will be apparent that various modifications can be made without departing from the spirit and scope of the invention. Accordingly, it is not intended that the invention be limited except as by the appended claims.

What is claimed is:

1. A balloon catheter device for abrading a patent foramen ovale comprising:

A a sheath catheter with proximal and distal ends;

B a foramen ovale balloon catheter deployably retained within the sheath catheter, the foramen ovale catheter having proximal and distal ends;

C an inflatable balloon attached near the distal end of the foramen ovale balloon catheter;

D a plurality of abrasive members attached over the inflatable balloon.

2. The catheter device of claim 1 wherein the abrasive members are a plurality of glue drops.

3. The catheter device of claim 1 wherein the abrasive members are a plurality of cylinders.

4. The catheter device of claim 1 wherein the abrasive members are a plurality of rectangular members.

5. The catheter device of claim 4 wherein the rectangular members have top and bottom corners and the wherein the bottom corners are rounded off.

6. The catheter device of claim 1 wherein the foramen ovale balloon catheter comprises an outer catheter and an inner catheter.

7. The catheter device of claim 6 wherein the inner catheter is longer than the outer catheter.

8. The catheter device of claim 7 wherein the balloon, outer catheter, and inner catheter all have proximal and distal ends and wherein the proximal end of the balloon is attached to the distal end of the outer catheter and wherein the distal end of the balloon is attached to the inner catheter.

9. The catheter device of claim 1 further comprising a plurality of wires attached over the balloon.

10. The catheter device of claim 9 wherein the wires are anchored via two rings, one on the proximal end of the balloon and the other on the distal end of the balloon.

11. The catheter device of claim 10 wherein the distal ring is free floating.

12. The catheter device of claim 1 further comprising a Y fitting attached to the proximal end of the foramen ovale balloon catheter.

13. A method of abrading a patent foramen ovale comprising the steps of:

A inserting an introducer catheter into a vessel of a patient with a patent foramen ovale;

B inserting a foramen ovale balloon catheter with proximal and distal ends and a balloon attached near its distal end and with a plurality of abrasive members attached over the balloon through the introducer catheter;

C advancing the foramen ovale balloon catheter through the patent foramen ovale;

D inflating the balloon;

E abrading the patent foramen ovale by manipulating the foramen ovale catheter such that the abrasive members abrade the lining of the foramen ovale;

F deflating the balloon; and

G removing the foramen ovale catheter and the introducer catheter from the patient.

14. The method of abrading a patent foramen ovale of claim 13 further comprising the step of inserting a sheath catheter through the introducer catheter.

15. The method of abrading a patent foramen ovale of claim 13 wherein the abrading is accomplished by translating the distal end of the foramen ovale catheter through the patent foramen ovale.

16. The method of abrading a patent foramen ovale of claim 13 wherein the abrading is accomplished by rotating the distal end of the foramen ovale catheter in the patent foramen ovale.

17. A method of training a person to perform the method of abrading a patent foramen ovale comprising the steps of demonstrating or instructing the performance of the method of claim 13.

18. The method of training a person of claim 17 further comprising the step of claim 14.

* * * * *